(12) United States Patent
Park et al.

(10) Patent No.: US 9,375,705 B2
(45) Date of Patent: Jun. 28, 2016

(54) HETEROGENEOUS COPPER NANOCATALYST AND MANUFACTURING METHODS THEREOF

(71) Applicant: Postech Academy-Industry Foundation, Pohang-si (KR)

(72) Inventors: Jai Wook Park, Pohang-si (KR); In Soo Park, Nam-gu (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 14/312,666

(22) Filed: Jun. 23, 2014

(65) Prior Publication Data

US 2014/0302984 A1 Oct. 9, 2014

Related U.S. Application Data

(62) Division of application No. 13/003,122, filed as application No. PCT/KR2008/004041 on Jul. 9, 2008, now Pat. No. 8,877,676.

(51) Int. Cl.

| B01J 23/70 | (2006.01) |
|---|---|
| B01J 23/72 | (2006.01) |
| B01J 35/00 | (2006.01) |
| B01J 37/03 | (2006.01) |
| B82Y 30/00 | (2011.01) |

(Continued)

(52) U.S. Cl.
CPC .............. *B01J 23/72* (2013.01); *B01J 35/0013* (2013.01); *B01J 37/033* (2013.01); *B82Y 30/00* (2013.01); *C07D 249/04* (2013.01); *B01J 21/04* (2013.01); *B01J 35/06* (2013.01); *B01J 35/1019* (2013.01); *B01J 35/1023* (2013.01)

(58) Field of Classification Search
CPC ................................ B01J 23/72; B01J 37/036
USPC ......................................................... 502/346
See application file for complete search history.

(56) References Cited

U.S. PATENT DOCUMENTS

| 5,128,307 A * | 7/1992 | Wanjek .................... B01J 23/72 502/342 |
|---|---|---|
| 5,935,889 A | 8/1999 | Murrell et al. |

(Continued)

FOREIGN PATENT DOCUMENTS

| JP | H09-163968 | 6/1997 |
|---|---|---|
| JP | 2005-034682 | 2/2005 |
| WO | 2010/005127 | 1/2010 |

OTHER PUBLICATIONS

International Search Report.

(Continued)

*Primary Examiner* — Cam N. Nguyen
(74) *Attorney, Agent, or Firm* — Steptoe & Johnson LLP (57) ABSTRACT

This invention relates to a heterogeneous copper nanocatalyst composed of copper nanoparticles immobilized on a boehmite support, a method of preparing the same, and the use thereof. The copper nanocatalyst composed of the copper nanoparticles supported on boehmite exhibits excellent performance in a Huisgen cycloaddition reaction and an A3 coupling reaction of aldehyde, amine and alkyne. The copper nanocatalyst is able to be prepared in a large scale and shows superior reactivity even when used in a small amount under mild conditions without an additive in an organic reaction. This heterogeneous catalyst is easy to separate and reuse after the reaction.

11 Claims, 4 Drawing Sheets

(51) Int. Cl.
 *C07D 249/04* (2006.01)
 *B01J 21/04* (2006.01)
 *B01J 35/06* (2006.01)
 *B01J 35/10* (2006.01)

(56) References Cited

U.S. PATENT DOCUMENTS

| | | | |
|---|---|---|---|
| 6,306,795 B1 * | 10/2001 | Ryan | B01J 23/72 423/604 |
| 6,472,561 B2 | 10/2002 | Ryan et al. | |
| 6,680,416 B1 * | 1/2004 | Hebgen | B01J 27/122 502/302 |
| 6,903,050 B2 * | 6/2005 | Ilinich | B01J 21/04 502/346 |
| 7,176,160 B2 | 2/2007 | Espinoza et al. | |
| 7,601,671 B2 * | 10/2009 | LaBarge | B01D 53/945 502/240 |
| 7,807,603 B2 * | 10/2010 | Schlitter | B01J 23/72 502/263 |
| 8,431,512 B2 * | 4/2013 | Egami | B01J 23/002 502/225 |
| 8,785,061 B2 * | 7/2014 | Yonemura | B01J 23/72 429/408 |
| 2004/0250827 A1 | 12/2004 | Deevi et al. | |
| 2005/0014938 A1 | 1/2005 | Gaster et al. | |
| 2009/0305872 A1 * | 12/2009 | Stamires | B01J 21/16 502/64 |

OTHER PUBLICATIONS

Office Action for Japanese Application No. 2011-517325, Jun. 4, 2012.

Kim, et al., Materials Chemistry and Physics, 104 (2007), 56-61.

* cited by examiner

FIG. 4

HETEROGENEOUS COPPER NANOCATALYST AND MANUFACTURING METHODS THEREOF

CLAIM OF PRIORITY

This application is a divisional of U.S. application Ser. No. 13/003,122, filed Mar. 24, 2011, now U.S. Pat. No. 8,877,676, which claims priority under 35 USC 371 to International Application No. PCT/KR2008/004041, filed on Jul. 9, 2008, which is incorporated by reference in its entirety.

TECHNICAL FIELD

The present invention relates to a heterogeneous copper nanocatalyst and a method of preparing the same, and more particularly to a heterogeneous nanocatalyst, which is composed of copper nanoparticles immobilized on a boehmite support, and to a method of preparing the same.

BACKGROUND ART

When metal particles are nano-sized, they are capable of exhibiting physical, chemical and optical properties which are not possessed by conventional bulk metal. In particular, concerning their application as catalysts, metal nanoparticles have a considerably large reactive surface area and surface specificity and thus manifest very high reactive activity which is not shown in general catalysts. However, because nanocatalysts may aggregate upon synthesis thereof and are not easy to prepare in a uniform size, they are mainly used in a state of being immobilized on activated carbon, inorganic oxide, polymer, zeolite, etc. Also, these catalysts have low reusability and are unsuitable for actual reactions because they have high catalytic reaction temperature or should be used in a large amount, and furthermore need a ligand such as ascorbic sodium or amine.

Meanwhile, a transition metal catalyst such as a palladium catalyst is utilized in various organic reactions (Negishi, E.-I. In Handbook of Organopalladium Chemistry for Organic Synthesis; Negishi, E., Ed.; John Wiley & Sons: New York, 2002). In particular, this catalyst is very effective for the reduction of alkenes or alkynes, oxidation of alcohol, olefinization of allyl halides or a carbon-carbon coupling reaction such as cross-coupling (Denmark, S. E.; Sweis, R. F. Acc. Chem. Res. 2002, 35, 835).

A homogenous catalyst which is typically used is difficult to separate or reuse, and incurs problems related to industrial applications thereof. In order to solve these problems, a heterogeneous catalyst is developing. Most heterogeneous catalysts are provided in the form in which palladium is immobilized on an inorganic support or an organic polymer (Djakovitch, L. et al., J. Am. Chem. Soc. 2001, 123, 5990). Furthermore, there are reported reusable heterogeneous catalysts including palladium nanoparticles, colloidal palladium, palladium entrapped in a polymer and so on (Kim, S.-W. et al., J. Am. Chem. Soc. 2002, 124, 7642; Roucoux, A. et al., Chem. Rev. 2002, 102, 3757; and Akiyama, R. et al., J. Am. Chem. Soc. 2003, 125, 3412). However, the aforementioned catalysts are problematic in terms of low reactivity, decomposition of the catalyst, leaching of the metal and complicated synthesis procedures.

Korean Unexamined Patent Publication No. 10-2006-0076419 discloses a method of preparing a heterogeneous transition metal catalyst including mixing a transition metal complex, a carrier precursor and a ligand for capturing metal thus preparing a mixture, and adding water to the mixture to induce a sol-gel reaction.

However, the palladium-based catalyst is undesirably expensive. Although the preparation of a catalyst using inexpensive metal continues, the catalyst thus prepared is problematic in that its activity is insufficient.

DISCLOSURE

Technical Problem

Accordingly, the present invention intends to provide a novel copper nanocatalyst having good catalytic activity.

Also the present invention intends to provide a method of preparing the copper nanocatalyst having good catalytic activity.

Also the present invention intends to provide use of the copper nanocatalyst having good catalytic activity.

Also the present invention intends to provide novel Huisgen reaction and A3 coupling reaction processes using the copper nanocatalyst having good catalytic activity.

Also the present invention intends to provide a novel compound prepared using the copper nanocatalyst.

Technical Solution

An aspect of the present invention provides a copper nanocatalyst composed of copper nanoparticles supported on boehmite.

In the present invention, boehmite may be provided in various forms able to support copper nanoparticles, and preferably, is provided in nanofibrous form so that copper nanoparticles supported thereon exhibit high activity.

In the present invention, the copper nanoparticles may have an average particle size of 1~10 nm and preferably 3~5 nm so as to exhibit high catalytic activity during the reaction. In an embodiment of the present invention, the copper nanoparticles may exist in various oxide forms while exhibiting the catalytic activity. For example, the inside or surface thereof may be composed of Cu, $Cu_2O$, CuO, or a mixture thereof.

In the present invention, the copper nanoparticles of the copper nanocatalyst are supported on boehmite in an amount of 0.1~20 wt %, preferably 1~10 wt %, and more preferably 4~5 wt %, based on the weight of boehmite.

In an embodiment of the present invention, the copper nanocatalyst may have a surface area of about 300~600 $m^2/g$, a pore volume of about 0.6~0.7 $cm^2/g$, and a pore size of about 3~4 nm, in order to manifest activity adapted for various chemical reactions.

Another aspect of the present invention provides a method of preparing the copper nanocatalyst, including adding a solution of a copper precursor with a boehmite precursor to allow the reaction to take place, thus obtaining a reaction product, and adding water to the reaction product to induce a sol-gel reaction.

In the present invention, the copper precursor may be selected from among $CuCl_2$, $Cu(NO_3)_2$, $CuSO_4$, CuI, CuCl and hydrates thereof, and is preferably $CuCl_2.2H_2O$. In addition, the use of two or more types of copper precursors is possible, and its hydrate precursor may be used as well.

In the present invention, the solution of the copper precursor may be prepared using an alcohol solvent able to dissolve the copper precursor at room temperature. The solvent may be selected from among ethanol, propanol, butanol, pentanol, hexanol, heptanol and octanol. Particularly useful is ethanol.

In an embodiment of the present invention, the alcohol solvent may be used in an amount 5~100 times, and preferably 30~40 times 1 g of the copper precursor.

In the present invention, the solution of the copper precursor preferably includes a size controller able to control the size of produced copper particles to a nano size. In an embodiment of the present invention, any size controller may be used as long as the size of resultant particles may be controlled to about 1~10 nm. Particularly useful is a non-ionic surfactant.

In the embodiment of the present invention, the non-ionic surfactant may include a non-ionic block copolymer represented by Formula 1 below.

Formula 1

In Formula 1, a, b and c each are an integer ranging from 10 to 100.

In a preferred embodiment of the present invention, a non-ionic block copolymer in which a and c are 20 and b is 70 may be used. The block copolymer for controlling the size of the particles is commercially available from BASF, and may include for example Pluronic P123.

In the embodiment of the present invention, the size controller may be used in an amount 1~1000 times, preferably 5~100 times, and more preferably 10~20 times the weight of the copper precursor.

In the present invention, the precursor of boehmite used as the carrier or support may be aluminum tri-sec-butoxide or aluminum tetra-i-propoxide. Particularly useful is aluminum tri-sec-butoxide.

In the present invention, the carrier precursor may be used in an amount 5~100 times, and preferably 20~50 times the weight of the copper precursor.

In an embodiment of the present invention, the solution of the copper precursor may be prepared by completely dissolving the size controller and the copper precursor at room temperature, adding the boehmite precursor thereto and then performing heating.

In the present invention, the reaction between the solution of the copper precursor and the boehmite precursor may be performed at 100~300° C., and preferably 150~200° C. The reaction time required for the completion of the reaction may vary depending on the reaction temperature and the concentration of reactants used, and is preferably set to about 6~12 hours.

In the present invention, a reducing agent for reducing the copper precursor may be selected from among hydrogen, metal hydride, and alcohol, including ethanol, n-butanol, sec-butanol or i-butanol.

In the present invention, the reaction product resulting from the reaction between the solution of the copper precursor and the boehmite precursor may be added with water, so that a sol-gel reaction occurs. As such, water may be used in an amount 1~100 times and preferably 2~10 times the weight of the carrier precursor.

The sol-gel reaction product may be filtered, washed using an appropriate solvent, and then dried, thereby simply obtaining a catalyst composed of immobilized copper nanoparticles according to the present invention.

A further aspect of the present invention provides use of the copper nanoparticles supported on the boehmite support as a catalyst. The nanoparticles according to the present invention have high reactivity. Even when this catalyst is reused ones of times after having been recovered, its superior catalytic activity is almost unchanged. Thus, the nanoparticles according to the present invention may be used as a catalyst for various chemical reactions including a Huisgen cycloaddition reaction and an A3 coupling reaction.

Still a further aspect of the present invention provides a Huisgen cycloaddition reaction for preparing a triazole compound from an alkyne compound and an azide compound using the copper nanocatalyst.

In the present invention, the copper nanocatalyst is a catalyst composed of copper nanoparticles supported on a boehmite support, in which the boehmite support is a fibrous support. In an embodiment of the present invention, the triazole compound may be produced from the alkyne and the azide in an organic solvent and an aqueous solvent mixture using the copper nanocatalyst. Preferably, the alkyne and the azide may be used at a ratio of 1:1.1 in the presence of 3.0 mol % copper nanocatalyst at room temperature. As such, the organic solvent may be n-hexane, and in the case of the aqueous solvent mixture, water and t-butanol may be used at a ratio of 1:1.

Still another aspect of the present invention provides a novel triazole compound prepared using the copper nanocatalyst.

Yet another aspect of the present invention provides an A3 coupling reaction of aldehyde, amine and alkyne in an organic solvent using the copper nanocatalyst.

In the present invention, the copper nanocatalyst is a catalyst composed of copper nanoparticles supported on a boehmite support. The boehmite support is a fibrous support. In an embodiment of the present invention, the ratio of aldehyde to amine to alkyne used for the above reaction may vary, and is preferably set to 1:1:1.5. The organic solvent used for the above reaction may be selected from among toluene, xylene, benzene, pentane and octane. Particularly useful is toluene. The reaction temperature may be 110° C. The amount of the copper nanocatalyst used for the above reaction may be 0.1~3 mol % but may vary depending on the types of alkyne, and is preferably set to 0.5 mol %.

A better understanding of the present invention may be obtained through the following examples which are set forth to illustrate, but are not to be construed as limiting the present invention.

Advantageous Effects

According to the present invention, a supported copper catalyst having high activity and a method of preparing the same were provided.

The copper nanocatalyst according to the present invention composed of copper nanoparticles supported on boehmite is very effective for Huisgen cycloaddition and A3 coupling. Also, this nanocatalyst can be easily produced in a large scale using inexpensive material. As well, unlike conventional catalysts, even when the copper nanocatalyst according to the present invention is used in a very small amount without an additive under mild conditions, it can show reactivity.

MODE FOR INVENTION

Example

Synthesis of Catalyst

Example 1

Preparation of Copper Nanocatalyst Immobilized on Boehmite

Figure 2:
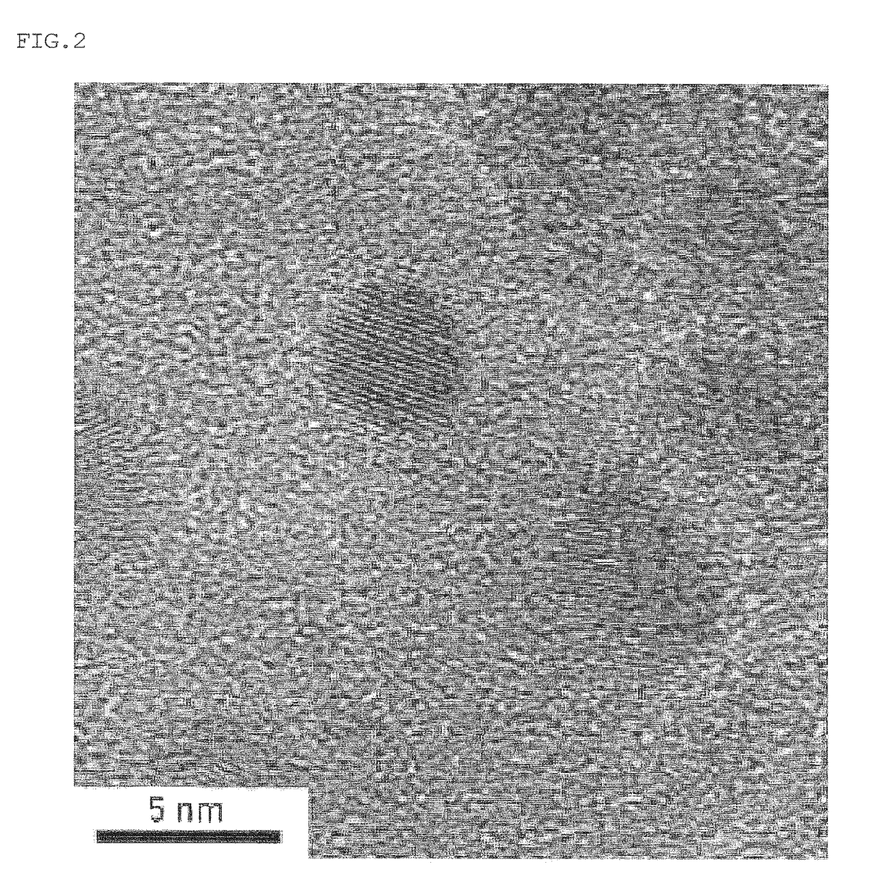
FIG. 2 is a low magnification image of FIG. 1.

In a 250 ml round-bottom flask as a reactor, 2 g of CuCl$_2$.2H$_2$O, 40 g of ethanol and 20 g of Pluronic P123 were stirred at room temperature for 30 min and thus sufficiently dissolved, after which the reactor was equipped with a reflux condenser and then placed in an oil bath at 160° C., and 50 g of aluminum tri-sec-butoxide was introduced into the reactor, followed by performing stirring for 8 hours. After the 8 hours, 20 ml of distilled water was added to the stirred solution, so that a sol-gel reaction was confirmed to occur. After 30 min, the reactor was removed from the oil bath and sufficiently cooled at room temperature. The reaction solution was washed with acetone using a glass filter (pore size=10~20 μl) until Pluronic P123 was sufficiently removed. The separated blue solid was sufficiently dried in an oven at 120° C. for 6 hours, thus obtaining a copper nanocatalyst (Cu/AlO(OH)) (18 g 4.3 w %) composed of immobilized yellowish green colored copper nanoparticles as shown in FIG. 2. The specific surface area of the catalyst was determined to be 360 m$^2$/g using a nitrogen adsorption isotherm.

Figure 1:
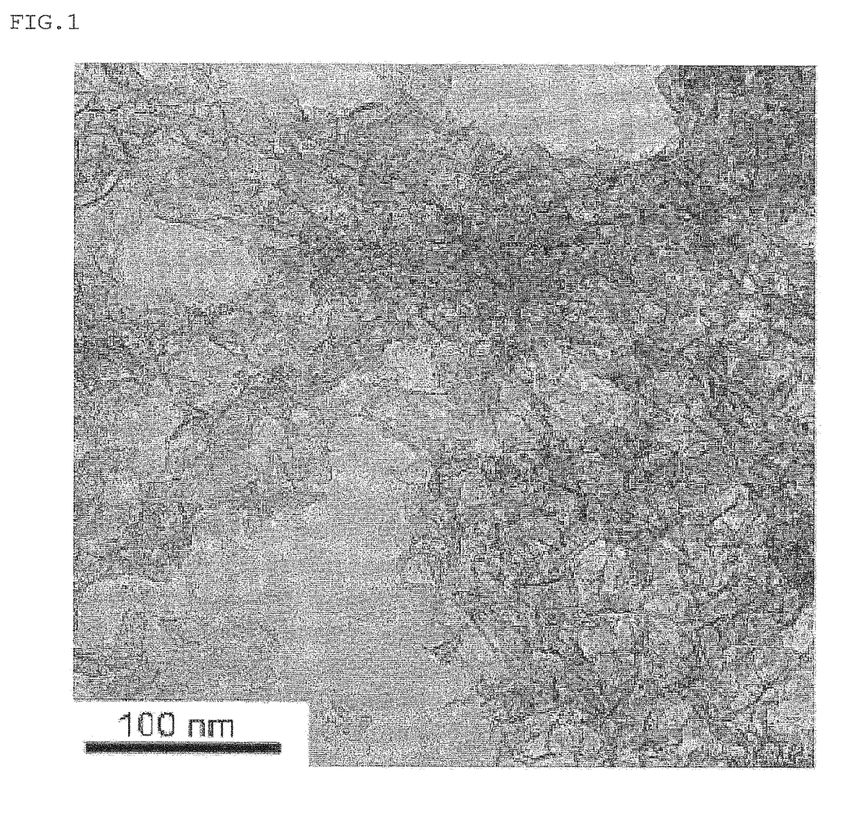
FIG. 1 is a transmission electron microscope (TEM) image of a copper nanocatalyst prepared in Example 1 according to the present invention.

The copper nanocatalyst immobilized on boehmite was observed using a TEM. The results are shown in FIG. 1. From (a) of FIG. 1, the boehmite fibers and the copper nanoparticles supported thereon could be seen. In a high resolution TEM (HR-TEM) image of (b), the crystal plane of the copper nanoparticles having a size of 3~5 nm could be seen.

Figure 3:
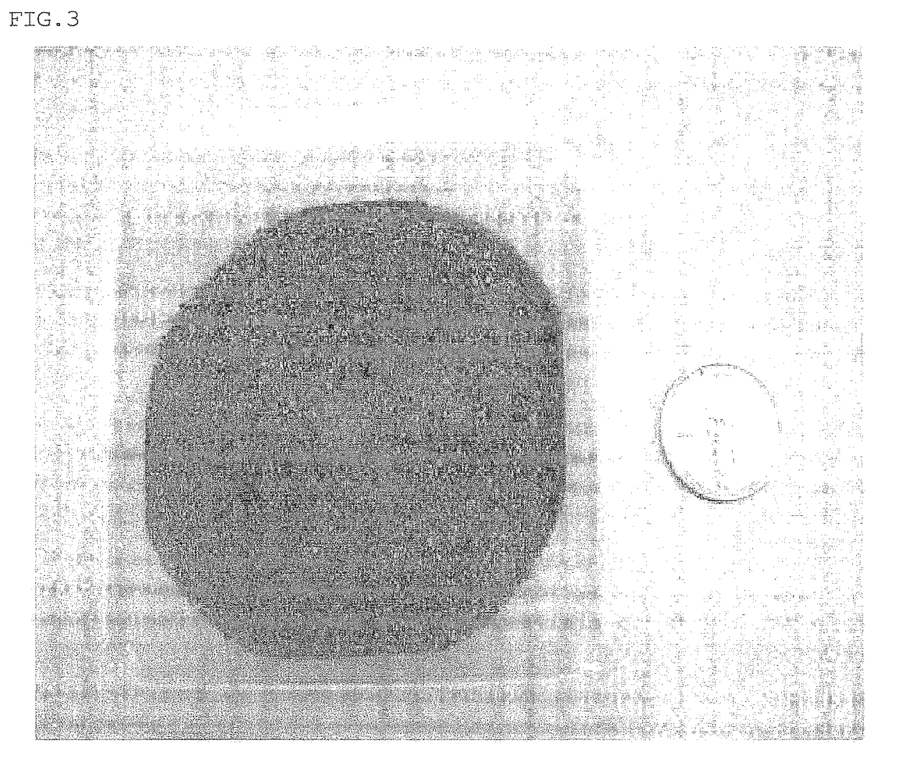
FIG. 3 is a photograph showing 20 g of the copper nanocatalyst prepared in Example 1 according to the present invention.
Figure 4:
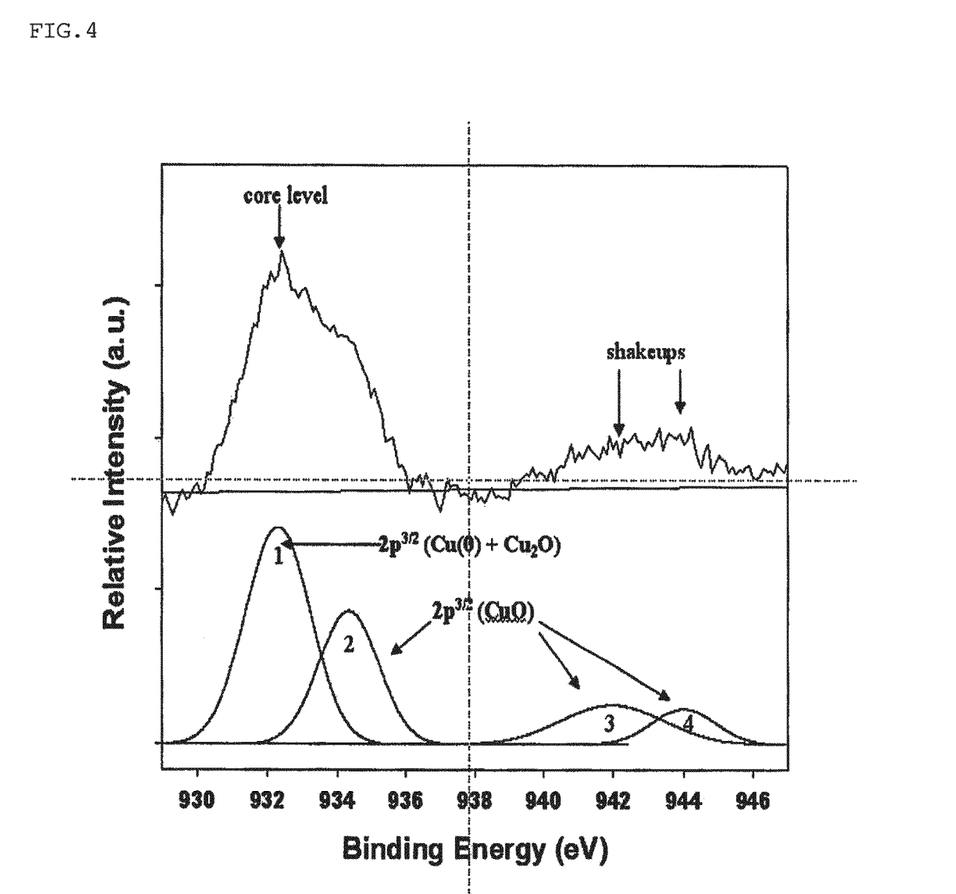
FIG. 4 is an X-ray photoelectron spectroscopic spectrum of the copper nanocatalyst prepared in Example 1 according to the preset invention, showing the state of oxidation of copper on the surface of the copper nanocatalyst.

Also, in order to determine the oxidation state of the copper nanocatalyst immobilized on boehmite, the oxidation state of the surface of copper was analyzed using X-ray photoelectron spectroscopy. As shown in the spectrum of FIG. 3, the relative quantitative ratios of (Cu+Cu$_2$O) and (CuO) could be determined.

Example 2

Into a reactor, phenylacetylene (1.0 mmol, 110 μl), benzyl azide (1.1 mmol, 155 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 6 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 225 mg (95% yield) of a desired triazole compound. Even when the separated catalyst was reused five times, its reactivity was almost unchanged.

Example 3

Into a reactor, phenylacetylene (1.0 mmol, 110 μl), octyl azide (1.1 mmol, 170 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 12 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 244 mg (95% yield) of a desired triazole compound, 1-octyl-4-phenyl-1H-1,2,3-triazole.

Example 4

Into a reactor, phenylacetylene (1.0 mmol, 110 μl), p-methoxyphenyl azide (1.1 mmol, 160 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 12 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 243 mg (97% yield) of a desired triazole compound, 1-(4-methoxyphenyl)-4-phenyl-1H-1,2,3-triazole.

Example 5

Into a reactor, 2-methyl-3-butyn-2-ol (1.0 mmol, 100 μl), octyl azide (1.1 mmol, 170 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 20 hours. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 226 mg (97% yield) of a desired triazole compound (liquid), 2-(1-octyl-1H-1,2,3-triazol-4-yl)propan-2-ol.

$^1$H NMR (300 MHz, CDCl$_3$) δ ppm 7.51 (s, 1H), 4.31 (t, 2H, J=7.26), 3.80 (s, 1H, OH), 1.89 (m, 2H, NCH$_2$), 1.63 (s, 6H), 1.40-1.20 (m, 10H), 0.87 (t, 3H, J=6.18) (75 MHz, CDCl$_3$) δ ppm 156.3, 119.7, 68.9, 50.8, 32.2, 31.0, 30.8, 29.5, 29.4, 27.0, 23.1, 14.5

HR FAB Mass: m/z 240.2080 (M+H), Calcd for m/z 240.2076 (M+H)

Example 6

Into a reactor, 2-methyl-3-butyn-2-ol (1.0 mmol, 100 μl), benzyl azide (1.1 mmol, 150 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 6 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 200 mg (92% yield) of a desired triazole compound, 2-(1-benzyl-1H-1,2,3-triazol-4-yl)propan-2-ol.

Example 7

Into a reactor, 2-methyl-3-butyn-2-ol (1.0 mmol, 100 μl), p-methoxyphenyl azide (1.1 mmol, 160 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 12 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 226 mg (97% yield) of a desired triazole compound, 2-(1-(4-methoxyphenyl-1H-1,2,3-triazol-4-yl)propan-2-ol.

$^1$H NMR (300 MHz, CDCl$_3$) δ ppm 7.86 (s, 1H), 7.59 (d, 2H, J=8.81), 6.98 (d, 2H, J=8.81), 3.85 (s, 3H, OCH$_3$), 3.25 (s, 1H, OH), 1.70 (s, 6H); $^{13}$C NMR (75 MHz, CDCl$_3$) δ ppm 160.3, 156.8, 131.2, 122.8, 118.5, 115.3, 69.2, 56.2, 31.1

LR FAB Mass: m/z 234.26 (M+H), m/z 256.25 (M+Na)

Elemental analysis: found C, 61.96; H, 6.46; N, 17.81. Calcd for C, 61.79; H, 6.48; N, 18.01

Example 8

Into a reactor, 2-phenyl-3-butyn-2-ol (1.0 mmol, 100 μl), p-methoxyphenyl azide (1.1 mmol, 160 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 12 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 286 mg (97% yield) of a desired triazole compound, 1-(1-(4-methoxyphenyl-1H-1,2,3-triazol-4-yl)-1-phenylethanol, as a white solid (mp: 142~143° C.)

$^1$H NMR (300 MHz, CDCl$_3$) δ ppm 7.68 (s, 1H), 7.60-7.50 (m, 4H), 7.40-7.20 (m, 3H), 6.98 (d, 2H, J=5.97), 3.84 (s, 3H, OCH$_3$), 3.28 (s, 1H, OH), 2.04 (s, 3H, CCH$_3$); $^{13}$C NMR (75 MHz, CDCl$_3$) δ ppm 160.4, 156.1, 147.0, 131.1, 128.9, 127.9, 125.9, 122.8, 119.7, 115.3, 72.8, 56.2, 31.3

LR FAB Mass: m/z 296.26 (M+H), m/z 329.20 (M+Na)

Elemental analysis: found C, 69.14; H, 5.80; N, 14.20. Calcd for C, 69.14; H, 5.80; N, 14.23

Example 9

Into a reactor, 1-ethynyl-1-cyclohexene (1.0 mmol, 120 μl), benzyl azide (1.1 mmol, 150 mg) and 3.0 ml of n-hexane were added and then the nanocatalyst (Cu/AlO(OH), 6.0 mol % 90 mg) composed of supported copper nanoparticles prepared in Example 1 was added. The copper nanocatalyst and the reactants were intensely stirred at room temperature for 24 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 185 mg (77% yield) of a desired triazole compound, 1-benzyl-4-cyclohexenyl-1H-1,2,3-triazole.

Example 10

Into a reactor, 1-octyne (1.0 mmol, 150 μl), benzyl azide (1.1 mmol, 150 mg) and 3.0 ml of n-hexane were added and then the nanocatalyst (Cu/AlO(OH), 6.0 mol % 90 mg) composed of supported copper nanoparticles prepared in Example 1 was added. The copper nanocatalyst and the reactants were intensely stirred at room temperature for 15 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 200 mg (82% yield) of a desired triazole compound, 1-benzyl-4-hexyl-1H-1,2,3-triazole.

Example 11

Into a reactor, ethyl propiolate (1.0 mmol, 103 μl), p-methoxyphenyl azide (1.1 mmol, 160 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 1 hour. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 240 mg (97% yield) of a desired triazole compound, ethyl 1-(4-methoxyphenyl)-1H-1,2,3-triazole-4-carboxylate (light yellow solid, mp 113~115° C.)

$^1$H NMR (300 MHz, CDCl$_3$) δ ppm 8.43 (s, 1H), 7.65 (d, 2H, J=6.83), 7.29 (d, 2H, J=9.03), 4.46 (q, 2H, J=14.3, COCH$_2$CH$_3$), 3.88 (s, 3H, OCH$_3$), 1.43 (t, 3H, J=7.15, COCH$_2$CH$_3$); $^{13}$C NMR (75 MHz, CDCl$_3$) δ ppm 161.3, 161.0, 141.3, 130.3, 126.2, 123.1, 115.5, 62.0, 56.3, 15.0

LR FAB Mass: m/z 248.23 (M+H), m/z 270.21 (M+Na)

Elemental analysis: found C, 58.34; H, 5.33; N, 16.98. Calcd for C, 58.29; H, 5.30; N, 16.99

Example 12

Into a reactor, p-fluorophenylacetylene (1.0 mmol, 116 μl), benzyl azide (1.1 mmol, 150 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 3 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 245 mg (97% yield) of a desired triazole compound, 1-benzyl-4-(4-fluorophenyl)-1H-1,2,3-triazole (white solid, mp: 113~115° C.).

$^1$H NMR (300 MHz, CDCl$_3$) δ ppm 7.80-7.68 (m, 2H), 7.63 (s, 1H), 7.40-7.22 (m, 5H), 7.12-7.02 (m, 2H), 5.55 (s, 2H, PhCH$_2$N); $^{13}$C NMR (75 MHz, CDCl$_3$) δ ppm 164.9, 161.6 (coupled with F), 148.0, 135.2, 129.8, 129.4 (coupled with F), 128.7, 128.1, 128.0, 127.5, 127.4 (coupled with F), 119.9, 116.5, 116.2 (coupled with F), 54.9

$^{19}$F NMR (300 MHz, CDCl$_3$) δ ppm-36.5

LR FAB Mass: m/z 254.25 (M+H), m/z 276.22 (M+Na)

Elemental analysis: found C, 70.89; H, 4.79; N, 16.52. Calcd for C, 71.13; H, 4.78; N, 16.59

Example 13

Into a reactor, propargyl ether (1.0 mmol, 100 μl), benzyl azide (2.2 mmol, 290 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 15 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 306 mg (85% yield) of a desired triazole compound, 4,4'-oxybis(methylene)bis(1-benzyl-1H-1,2,3-triazole).

$^1$H NMR (300 MHz, CDCl$_3$) δ ppm 7.48 (s, 2H), 7.40-7.26 (m, 6H), 7.25-7.18 (m, 4H), 5.45 (s, 4H, PhCH$_2$N), 4.65 (s, 4H); $^{13}$C NMR (75 MHz, CDCl$_3$) δ ppm 145.5, 135.1, 129.7, 129.3, 128.7, 123.3, 64.2, 54.7

LR FAB Mass: m/z 361.14 (M+H), m/z 383.11 (M+Na)

Elemental analysis: found C, 66.70; H, 5.56; N, 23.08. Calcd for C, 66.65; H, 5.59; N, 23.32

Example 14

Into a reactor, 1,6-heptadiyne (1.0 mmol, 120 μl), benzyl azide (2.2 mmol, 290 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 15 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 303 mg (85% yield) of a desired triazole compound, 1,3-bis(1-benzyl-1H-1,2,3-triazol-4-yl)propane (white solid, mp: 129~130° C.).

$^1$H NMR (300 MHz, CDCl$_3$) δ ppm 7.40-7.28 (m, 6H), 7.25-7.20 (m, 6H), 5.46 (s, 4H, PhCH$_2$N), 2.72 (t, 4H, J=7.38), 2.00 (m, 2H); $^{13}$C NMR (75 MHz, CDCl$_3$) δ ppm 148.5, 135.4, 129.6, 129.1, 128.5, 121.4, 54.5, 29.5, 25.5

LR FAB Mass: m/z 359.23 (M+H), m/z 381.22 (M+Na)

Elemental analysis: found C, 70.28; H, 6.08; N, 23.27. Calcd for C, 70.37; H, 6.19; N, 23.45

Example 15

Into a reactor, 2-ethynylpyridine (1.0 mmol, 105 μl), p-methoxyphenyl azide (1.1 mmol, 160 mg) and 3.0 ml of n-hexane were added and then the nanocatalyst (Cu/AlO (OH), 3.0 mol % 45 mg) composed of supported copper nanoparticles prepared in Example 1 was added. The copper nanocatalyst and the reactants were intensely stirred at room temperature for 3 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 248 mg (98% yield) of a desired triazole compound, 2-(1-(4-methoxyphenyl)-1H-1,2,3-triazol-4-yl)pyridine (bright yellow solid, mp: 129~130° C.).

$^1$H NMR (300 MHz, CDCl$_3$) δ ppm 8.61 (d, 2H, J=4.12), 8.51 (s, 1H), 8.24 (d, 1H, J=7.91), 7.80 (t, 1H, J=6.04), 7.70 (d, 2H, J=9.00), 7.25 (m, 1H), 7.03 (d, 2H, J=9.00), 3.85 (s, 3H, OCH$_3$); $^{13}$C NMR (75 MHz, CDCl$_3$) δ ppm 160.5, 150.7, 150.1, 149.3, 137.5, 131.0, 123.6, 122.6, 121.0, 120.7, 115.4, 56.2

LR FAB Mass: m/z 253.25 (M+H), m/z 275.23 (M+Na)

Elemental analysis: found C, 66.46; H, 4.93; N, 22.05. Calcd for C, 66.65; H, 4.79; N, 22.21

Example 16

Into a reactor, 2-ethynylpyridine (1.0 mmol, 105 μl), benzyl azide (1.1 mmol, 150 mg) and 3.0 ml of n-hexane were added and then the nanocatalyst (Cu/AlO(OH), 3.0 mol % 45 mg) composed of supported copper nanoparticles prepared in Example 1 was added. The copper nanocatalyst and the reactants were intensely stirred at room temperature for 3 hours. The production of an opaque white solid in the transparent solution with the passage of time was observed with the naked eye. After the reaction, the reaction product was dissolved in ethylacetate, and then the catalyst was separated using a glass filter. The solvent was removed, after which the obtained product was passed through a silica gel column (eluent: hexane/ethylacetate (2/1)), thus obtaining 230 mg (97% yield) of a desired triazole compound, 2-(1-benzyl-1H-1,2,3-triazol-4-yl)pyridine.

TABLE 1

| Ex. | Alkyne | Azide | Time (h) | Product | Yield (%) |
|---|---|---|---|---|---|
| 3 | Ph—≡ | n-octylazide | 12 | 1-n-octyl-4-phenyl-1H-1,2,3-triazole | 95% |
| 4 | Ph—≡ | 4-methoxyphenyl azide | 12 | 1-(4-methoxyphenyl)-4-phenyl-1H-1,2,3-triazole | 97% |
| 5 | 2-methyl-3-butyn-2-ol | n-octylazide | 20 | 2-(1-n-octyl-1H-1,2,3-triazol-4-yl)propan-2-ol | 97% |
| 6 | 2-methyl-3-butyn-2-ol | benzyl azide | 6 | 2-(1-benzyl-1H-1,2,3-triazol-4-yl)propan-2-ol | 92% |
| 7 | 2-methyl-3-butyn-2-ol | 4-methoxyphenyl azide | 12 | 2-(1-(4-methoxyphenyl)-1H-1,2,3-triazol-4-yl)propan-2-ol | 97% |
| 8 | 2-phenyl-3-butyn-2-ol | 4-methoxyphenyl azide | 12 | 2-(1-(4-methoxyphenyl)-1H-1,2,3-triazol-4-yl)-2-phenylethanol | 97% |
| 9 | 1-ethynylcyclohexene | benzyl azide | 24 | 1-benzyl-4-(cyclohex-1-en-1-yl)-1H-1,2,3-triazole | 77% |
| 10 | n-Hexyl—≡ | benzyl azide | 16 | 1-benzyl-4-n-hexyl-1H-1,2,3-triazole | 82% |
| 11 | ethyl propiolate | 4-methoxyphenyl azide | 1 | ethyl 1-(4-methoxyphenyl)-1H-1,2,3-triazole-4-carboxylate | 97% |

TABLE 1-continued

| Ex. | Alkyne | Azide | Time (h) | Product | Yield (%) |
|---|---|---|---|---|---|
| 12 | 4-fluorophenylacetylene | N₃-CH₂-Ph | 3 | 1-benzyl-4-(4-fluorophenyl)-1H-1,2,3-triazole | 97% |
| 13 | dipropargyl ether | N₃-CH₂-Ph | 10 | bis-triazole with OCH₂ linker | 85% |
| 14 | 1,6-heptadiyne | N₃-CH₂-Ph | 16 | bis-triazole with CH₂ linker | 85% |
| 15 | 2-ethynylpyridine | 4-methoxyphenyl azide | 3 | 1-(4-methoxyphenyl)-4-(pyridin-2-yl)-1H-1,2,3-triazole | 98% |
| 16 | 2-ethynylpyridine | N₃-CH₂-Ph | 3 | 1-benzyl-4-(pyridin-2-yl)-1H-1,2,3-triazole | 97% |

Example 17

Benzaldehyde (1.00 mmol, 100 μl), morpholine (1.0 mmol, 100 μl) and phenylacetylene (1.5 mmol, 170 μl) were introduced into a reactor along with 3.0 in of toluene, and the nanocatalyst (Cu/AlO(OH), 0.5 mol % 7.3 mg) composed of immobilized copper nanoparticles prepared in Example 1 was then added thereto, after which this mixture was stirred at not for 3 hours. After the reaction, the resulting product was passed through a silica gel column (eluent: hexane/ethylacetate (15:1)), thus obtaining 263 mg (95% yield) of a desired propargyl-coupled compound.

Example 18

Cyclohexane carboxyaldehyde (1.00 mmol, 120 μl), morpholine (1.0 mmol, 90 μl) and phenylacetylene (1.5 mmol, 170 μl) were introduced into a reactor along with 3.0 ml of toluene, and the nanocatalyst (Cu/AlO(OH), 0.5 mol % 7.3 mg) composed of immobilized copper nanoparticles prepared in Example 1 was then added thereto, after which this mixture was stirred at 110° C. for 2 hours. After the reaction, the resulting product was passed through a silica gel column (eluent: hexane/ethylacetate (15:1)), thus obtaining 278 mg (98% yield) of a desired propargyl-coupled compound.

Example 19 p-Bromobenzaldehyde (1.00 mmol, 190 mg), morpholine (1.0 mmol, 90 μl) and phenylacetylene (1.5 mmol, 170 μl) were introduced into a reactor along with 3.0 ml of toluene, and the nanocatalyst (Cu/AlO(OH), 0.5 mol % 7.3 mg) composed of immobilized copper nanoparticles prepared in Example 1 was then added thereto, after which this mixture was stirred at 110° C. for 3 hours. After the reaction, the resulting product was passed through a silica gel column (eluent: hexane/ethylacetate (15:1)), thus obtaining 320 mg (90% yield) of a desired propargyl-coupled compound.

Example 20

2-Bromobenzaldehyde (1.00 mmol, 116 μl), morpholine (1.0 mmol, 90 μl) and phenylacetylene (1.5 mmol, 170 μl) were introduced into a reactor along with 3.0 ml of toluene, and the nanocatalyst (Cu/AlO(OH), 0.5 mol % 7.3 mg) composed of immobilized copper nanoparticles prepared in Example 1 was then added thereto, after which this mixture was stirred at 110° C. for 3 hours. After the reaction, the resulting product was passed through a silica gel column (eluent: hexane/ethylacetate (15:1)), thus obtaining 340 mg (95% yield) of a desired propargyl-coupled compound.

Example 21

3,5-di-t-Butyl-2-hydroxybenzaldehyde (1.00 mmol, 234 mg), morpholine (1.0 mmol, 90 μl) and phenylacetylene (1.5 mmol, 170 μl) were introduced into a reactor along with 3.0 ml of toluene, and the nanocatalyst (Cu/AlO(OH), 1.0 mol % 15 mg) composed of immobilized copper nanoparticles prepared in Example 1 was then added thereto, after which this mixture was stirred at 110° C. for 12 hours. After the reaction, the resulting product was passed through a silica gel column (eluent: hexane/ethylacetate (15:1)), thus obtaining 315 mg (78% yield) of a desired propargyl-coupled compound.

Example 22

Benzaldehyde (1.00 mmol, 100 μl), morpholine (1.0 mmol, 90 μl) and 4-pentyn-1-ol (1.5 mmol, 140 μl) were introduced into a reactor along with 3.0 ml of toluene, and the nanocatalyst (Cu/AlO(OH), 3.0 mol % 50 mg) composed of immobilized copper nanoparticles prepared in Example 1 was then added thereto, after which this mixture was stirred at 110° C. for 12 hours. After the reaction, the resulting product was passed through a silica gel column (eluent: hexane/ethylacetate (10:1)), thus obtaining 195 mg (75% yield) of a desired propargyl-coupled compound.

Example 23

Benzaldehyde (1.00 mmol, 100 μl), morpholine (1.0 mmol, 90 μl) and 1-ethynyl-1-cyclohexene (1.5 mmol, 180 μl) were introduced into a reactor along with 3.0 ml of toluene, and the nanocatalyst (Cu/AlO(OH), 3.0 mol % 50 mg) composed of immobilized copper nanoparticles prepared in Example 1 was then added thereto, after which this mixture was stirred at 110° C. for 12 hours. After the reaction, the resulting product was passed through a silica gel column (eluent: hexane/ethylacetate (10:1)), thus obtaining 233 mg (83% yield) of a desired propargyl-coupled compound.

Example 24

Benzaldehyde (1.00 mmol, 100 μl), morpholine (1.0 mmol, 90 μL) and 2-methyl-3-butyn-2-ol (1.5 mmol, 150 μl) were introduced into a reactor along with 3.0 ml of toluene, and the nanocatalyst (Cu/AlO(OH), 3.0 mol % 50 mg) composed of immobilized copper nanoparticles prepared in Example 1 was then added thereto, after which this mixture was stirred at 110° C. for 12 hours. After the reaction, the resulting product was passed through a silica gel column (eluent: hexane/ethylacetate (10:1)), thus obtaining 210 mg (81% yield) of a desired propargyl-coupled compound.

Example 25 trans-Cinnamaldehyde (1.00 mmol, 130 μl), morpholine (1.0 mmol, 90 μl) and phenylacetylene (1.5 mmol, 170 μl) were introduced into a reactor along with 3.0 ml of toluene, and the nanocatalyst (Cu/AlO(OH), 0.50 mol % 7.3 mg) composed of immobilized copper nanoparticles prepared in Example 1 was then added thereto, after which this mixture was stirred at 110° C. for 12 hours. After the reaction, the resulting product was passed through a silica gel column (eluent: hexane/ethylacetate (10:1)), thus obtaining 275 mg (91% yield) of a desired propargyl-coupled compound.

Example 26

Benzaldehyde (1.00 mmol, 100 μl), morpholine (1.0 mmol, 90 μl) and 1-octyne (1.5 mmol, 230 μl) were introduced into a reactor along with 3.0 ml of toluene, and the nanocatalyst (Cu/AlO(OH), 6.0 mol % 100 mg) composed of immobilized copper nanoparticles prepared in Example 1 was then added thereto, after which this mixture was stirred at 110° C. for 15 hours. After the reaction, the resulting product was passed through a silica gel column (eluent: hexane/ethylacetate (10:1)), thus obtaining 269 mg (94% yield) of a desired propargyl-coupled compound.

Example 27 trans-Cinnamaldehyde (1.00 mmol, 130 μl), morpholine (1.0 mmol, 90 μl) and p-ethynylanisole (1.5 mmol, 200 μl) were introduced into a reactor along with 3.0 ml of toluene, and the nanocatalyst (Cu/AlO(OH), 0.50 mol % 7.6 mg) composed of immobilized copper nanoparticles prepared in Example 1 was then added thereto, after which this mixture was stirred at 110° C. for 3 hours. After the reaction, the resulting product was passed through a silica gel column (eluent: hexane/ethylacetate (10:1)), thus obtaining 316 mg (95% yield) of a desired propargyl-coupled compound.

Example 28 trans-Cinnamaldehyde (1.00 mmol, 130 μl), morpholine (1.0 mmol, 90 μl) and trimethylsilylacetylene (1.5 mmol, 220 μl) were introduced into a reactor along with 3.0 ml of toluene, and the nanocatalyst (Cu/AlO(OH), 3.0 mol % 50 mg) composed of immobilized copper nanoparticles prepared in Example 1 was then added thereto, after which this mixture was stirred at 110° C. for 12 hours. After the reaction, the resulting product was passed through a silica gel column (eluent: hexane/ethylacetate (10:1)), thus obtaining 250 mg (83% yield) of a desired propargyl-coupled compound.

Example 29 trans-Cinnamaldehyde (1.00 mmol, 130 μl), morpholine (1.0 mmol, 90 μl) and 4-ethynylphenylacetonitrile (1.5 mmol, 230 μl) were introduced into a reactor along with 3.0 ml of toluene, and the nanocatalyst (Cu/AlO(OH), 0.50 mol % 7.3 mg) composed of immobilized copper nanoparticles prepared in Example 1 was then added thereto, after which this mixture was stirred at 110° C. for 3 hours. After the reaction, the resulting product was passed through a silica gel column (eluent: hexane/ethylacetate (10:1)), thus obtaining 320 mg (94% yield) of a desired propargyl-coupled compound.

Example 30 trans-Cinnamaldehyde (1.00 mmol, 130 μl), morpholine (1.0 mmol, 90 μl) and 2-ethynyl-6-methoxynaphthalene (1.5 mmol, 280 mg) were introduced into a reactor along with 3.0 ml of toluene, and the nanocatalyst (Cu/AlO(OH), 0.50 mol % 7.3 mg) composed of immobilized copper nanoparticles prepared in Example 1 was then added thereto, after which this mixture was stirred at 110° C. for 3 hours. After the reaction, the resulting product was passed through a silica gel column (eluent: hexane/ethylacetate (10:1)), thus obtaining 340 mg (89% yield) of a desired propargyl-coupled compound.

The reactants and product of Examples 18 to 30 are shown in Tables 2 and 3 below.

TABLE 2

| Ex. | Aldehyde | Amine | Alkyne | Time (h) | Product | Yield (%) |
|---|---|---|---|---|---|---|
| 18 | cyclohexyl-CHO | morpholine (HN-morpholine) | Ph—≡ | 2 | 1-cyclohexyl-1-morpholino-3-phenyl-2-propyne | 98% |
| 19 | 4-bromobenzaldehyde | morpholine | Ph—≡ | 3 | 1-(4-bromophenyl)-1-morpholino-3-phenyl-2-propyne | 90% |
| 20 | 2-bromobenzaldehyde | morpholine | Ph—≡ | 3 | 1-(2-bromophenyl)-1-morpholino-3-phenyl-2-propyne | 95% |
| 21 | 3,5-di-tert-butyl-2-hydroxybenzaldehyde | morpholine | Ph—≡ | 12 | 2-(1-morpholino-3-phenylprop-2-yn-1-yl)-4,6-di-tert-butylphenol | 78% |

TABLE 2-continued

| Ex. | Aldehyde | Amine | Alkyne | Time (h) | Product | Yield (%) |
|---|---|---|---|---|---|---|
| 22 |  |  |  | 12 |  | 75% |
| 23 |  |  |  | 12 |  | 83% |
| 24 |  |  |  | 12 |  | 81% |
| 25 |  |  | Ph—≡ | 3 |  | 91% |

TABLE 3

| Ex. | Aldehyde | Amine | Alkyne | Time (h) | Product | Yield(%) |
|---|---|---|---|---|---|---|
| 26 |  |  | n-hexyl—≡ | 15 |  | 94% |

TABLE 3-continued

| Ex. | Aldehyde | Amine | Alkyne | Time (h) | Product | Yield(%) |
|---|---|---|---|---|---|---|
| 27 | cinnamaldehyde | morpholine | MeO-C6H4-C≡CH | 3 | morpholine-CH(C≡C-C6H4-OMe)-CH=CH-Ph | 95% |
| 28 | cinnamaldehyde | morpholine | TMS-C≡CH | 3 | morpholine-CH(C≡C-TMS)-CH=CH-Ph | 83% |
| 29 | cinnamaldehyde | morpholine | NC-CH2-C6H4-C≡CH | 3 | morpholine-CH(C≡C-C6H4-CH2CN)-CH=CH-Ph | 94% |
| 30 | cinnamaldehyde | morpholine | HC≡C-naphthyl-OMe | 3 | morpholine-CH(C≡C-naphthyl-OMe)-CH=CH-Ph | 89% |

The invention claimed is:

1. A method of preparing a catalyst, comprising reacting a solution of a copper precursor with a boehmite precursor, thus obtaining a reaction product, and then adding water to the reaction product so that a sol-gel reaction occurs, wherein the solution of the copper precursor comprises a size controller for controlling a size of copper particles to a nano size.

2. The method according to claim 1, wherein the copper precursor is $CuCl_2$, $Cu(NO_3)_2$, $CuSO_4$, CuI, CuCl, a mixture of two or more thereof, or a hydrate thereof.

3. The method according to claim 1, wherein the solution of the copper precursor is prepared using an alcohol solvent.

4. The method according to claim 3, wherein the alcohol solvent is used in an amount 5-100 times a weight of the copper precursor.

5. The method according to claim 1, wherein the size controller is a non-ionic surfactant.

6. The method according to claim 5, wherein the non-ionic surfactant is a non-ionic block copolymer represented by Formula 1 below:

HO(C$_2$H$_4$O)$a$(—C$_3$H$_6$O)$b$(C$_2$H$_4$O)$c$H     Formula 1 wherein a, b and c each are an integer ranging from 10 to 100.

7. The method according to claim 5, wherein the size controller is used in an amount of 1-1000 times a weight of the copper precursor.

8. The method according to claim 1, wherein the boehmite precursor is aluminum tri-sec-butoxide, aluminum tetra-i-propoxide or a mixture thereof.

9. The method according to claim 8, wherein the boehmite precursor is used in an amount 5-100 times a weight of the copper precursor.

10. The method according to claim 1, wherein the solution of the copper precursor is prepared by completely dissolving the size controller and the copper precursor at room temperature, adding the boehmite precursor thereto and then performing heating.

11. The method according to claim 1, wherein a reaction between the copper precursor and the boehmite occurs at 100-300° C.

* * * * *